(12) United States Patent
Fuentes

(10) Patent No.: US 6,306,139 B1
(45) Date of Patent: Oct. 23, 2001

(54) INTERVERTEBRAL CONNECTION DEVICE WITH AN ANTI-EXTRACTION DEVICE TO PREVENT EXTRACTION OF ANCHORING SCREWS

(75) Inventor: Jean-Marc Fuentes, Montpellier (FR)

(73) Assignee: Scint'x, Paris (FR)

( * ) Notice: Subject to any disclaimer, the term of this patent is extended or adjusted under 35 U.S.C. 154(b) by 0 days.

(21) Appl. No.: 09/271,287

(22) Filed: Mar. 17, 1999

(30) Foreign Application Priority Data

Oct. 19, 1998 (FR) .................................................. 98 13 224

(51) Int. Cl.[7] .................................................... A61B 17/80
(52) U.S. Cl. .................................. 606/70; 606/69; 606/61
(58) Field of Search ................................. 606/61, 69, 70, 606/71; 623/17, 17.11; 411/356, 81, 85, 102, 965; 70/455, 450; 285/81, 87, 90, 91; 220/241, 242

(56) References Cited

U.S. PATENT DOCUMENTS 4,794,918 * 1/1989 Wolter ...................................... 606/71
5,951,558 * 9/1999 Fiz ........................................... 606/70

FOREIGN PATENT DOCUMENTS 0 599 640 A1    6/1994 (EP).
2 740 321       4/1997 (FR).
WO 98/34553     8/1998 (WO).

* cited by examiner

Primary Examiner—David O. Reip
Assistant Examiner—Julian W. Woo
(74) Attorney, Agent, or Firm—Bacon & Thomas, PLLC

(57) ABSTRACT

An intervertebral connection device having a rigid osteosynthesis plate adapted to cover outer faces of at least two consecutive vertebrae at least partially. The plate includes an anterior face and an opposite posterior face. The posterior face is positionable against outer faces of at least two consecutive vertebrae. The plate further includes at least one pair of through bores each adapted to receive an anchoring screw arranged to anchor the plate on a vertebrae. The anchoring screws each includes a screw head. An anti-extraction device is adapted to prevent extraction of the anchoring screws. The anti-extraction device is mounted on the anterior face of the plate and acts as stops for the screw heads of the anchoring screws. The anti-extraction device includes at least one mobile flap mounted on the plate by a guide device. The anti-extraction device is movable between a first position that permits access to the through bores and a second position that obturates access to the through bores at least partially to act as stops for the screw heads.

22 Claims, 3 Drawing Sheets

INTERVERTEBRAL CONNECTION DEVICE WITH AN ANTI-EXTRACTION DEVICE TO PREVENT EXTRACTION OF ANCHORING SCREWS

FIELD OF THE INVENTION

The present invention relates to intervertebral connection devices designed to correct a weakening, a fracture of the vertebrae, or a defective posture of the spine.

It relates more precisely to devices for connecting the cervical vertebrae, preferably intended to be fixed on their anterior face.

BACKGROUND OF THE INVENTION

An anterior intervertebral connection device generally comprises a rigid osteosynthesis plate adapted to cover at least partially two consecutive vertebrae, in order to join them together. This osteosynthesis plate presents an anterior face and an opposite posterior face intended to be applied against the anterior face of the vertebrae. This plate is generally provided with two pairs of through holes, designed each to receive a screw intended to be anchored in the body of the vertebrae.

After implantation of such osteosythsis devices in patients, a phenomenon of avulsion or of partial extraction of the anchoring screws has been observed. This results in a risk of lesion or injury, particularly of the oesophagus and the pharynx.

The need is therefore felt to ensure blocking of the anchoring screws in order to avoid their leaving the osteosynthesis plate.

In an attempt to satisfy this need, document FR 2 740 321 has proposed an osteosynthesis device comprising, as means preventing extraction of the screws, a rigid counter-plate intended to be fixed on the anterior face of the osteosynthesis plate. The shape of this counter-plate is substantially similar to that of the osteosynthesis plate, so as to totally to cover all the anchoring screw heads. The counter-plate is fixed on the osteosynthesis plate with the aid of a screw adapted to screw in a tapping made on the osteosynthesis plate. The counter-plate thus constitutes a stop for the heads of the screws.

It must be considered that the operation of positioning these anti-extraction means is relatively long to carry out due to the phase of positioning of the counter-plate, followed by a phase of screwing the counter-plate on the osteosynthesis plate. Furthermore, the screw for fixing the counter-plate on the osteosynthesis plate risks unscrewing, resulting in the counter-plate moving away from the plate and thus in an avulsion of the anchoring screws. Moreover, it must be considered that the use of a rigid counter-plate presents relatively large dimensions capable of causing injuries or lesions.

It is therefore an object of the invention to overcome the drawbacks set forth hereinabove by proposing an intervertebral connection device designed to present an efficient and reliable means for blocking the anchoring screws, while being easy and quick to place in position.

SUMMARY OF THE INVENTION

The invention relates to an intervertebral connection device comprising a rigid osteosynthesis plate adapted to cover outer faces of at least two consecutive vertebrae at least partially. The plate comprises an anterior face and an opposite posterior face. The posterior face is positionable against outer faces of at least two consecutive vertebrae. The plate further comprises at least one pair of through bores each adapted to receive an anchoring screw arranged to anchor the plate on a vertebrae. The anchoring screws each comprise a screw head. An anti-extraction device is adapted to prevent extraction of the anchoring screws. The anti-extraction device is mounted on the anterior face of the plate and acts as stops for the screw heads of the anchoring screws. The anti-extraction device comprises at least one mobile flap mounted on the plate by a guide device. The anti-extraction device is movable between a first position that permits access to the through bores and a second position that obturates access to the through bores at least partially to act as stops for the screw heads.

BRIEF DESCRIPTION OF THE DRAWINGS

The invention will be more readily understood by reading the following description of embodiments thereof, given by way of non-limiting example and with reference to the accompanying drawings, in which.

DESCRIPTION OF THE PREFERRED EMBODIMENTS

Figure 1:
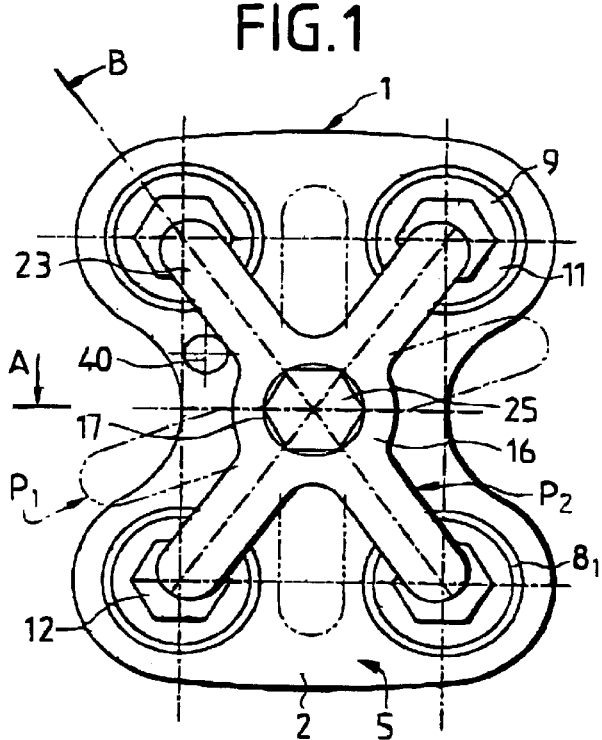
FIG. 1 is a front view of an intervertebral connection device according to the invention.
Figure 2:
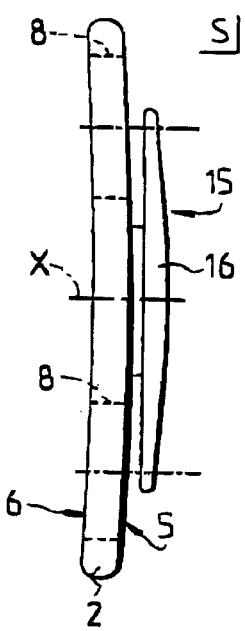
FIG. 2 is a side view of the intervertebral connection device according to the invention.
Figure 3:
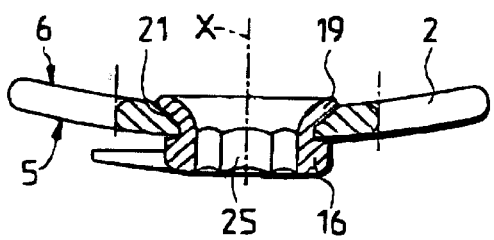
FIG. 3 is a transverse section taken substantially alone line A of FIG. 1.
Figure 4:
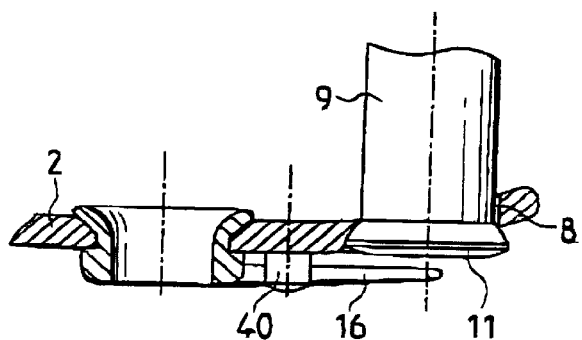
FIG. 4 is a view in section taken substantially along line B of FIG. 1 and showing a detail of embodiment of the object of the invention.

Referring now to the drawings, FIG. 1 to 4 illustrate a first embodiment of an osteosynthesis or intervertebral connection device 1 adapted to be mounted on the outer face of the cervical vertebrae. According to this first embodiment, the connection device 1 comprises an osteosynthesis or rigid connection plate 2 adapted to cover at least partially two consecutive or contiguous vertebrae (not shown). The connection plate 2 comprises an anterior face 5 and an opposite or posterior face 6 intended to be applied against the outer face of the vertebrae, namely the anterior face in the example illustrated. Of course, the connection plate 2 maybe mounted differently, for example laterally on the vertebrae.

The connection plate 2 presents a small thickness, for example of the order of 1 mm, and is made of a rigid material, such as titanium or other metals, or polymer. As is shown more precisely in FIG. 2, the connection plate 2 preferably presents, in the sagittal plane S considered as the plane of the sheet according to FIG. 2, a curvature adapted to the profile of the contiguous vertebrae to be assembled. In the same sense, the connection plate 2 presents, in a cross section transverse with respect to the sagittal plane S (FIG. 3), a curvature concave along the posterior face 6.

The plate 2 comprises at least one end, in the embodiment illustrated, two pairs of holes 8 each extending opposite one of the bones or the two vertebrae 3 and 4. Each hole 8 is intended to receive an anchoring screw 9 screwed in the corresponding vertebra by applying the posterior face 6 of the connection plate 2 against the outer face of the vertebrae. Each anchoring screw 9 is conventionally provided with a widened head 11 intended to be housed inside a dish $8_f$ of the hole 8, opening from the anterior face 5 of the plate 2. Moreover, each head 11 of an anchoring screw comprises a hexagonal orifice 12 for screwing or unscrewing.

The connection device 1 also comprises an anti-extraction device 15 preventing extraction of the anchoring screws 9. According to the invention, the anti-extraction device 15 is constituted by at least one mobile flap 16 mounted on the anterior face 5 of the plate 2 via a guide device 17 for positioning the mobile flap 16. The mobile flap 16 is adapted in order, in a first position $P_1$, shown in dot-and-ash lines in FIG. 1, to free the cross-section of passage of the holes 8 and, in a second position $P_2$, as illustrated in FIG. 1, to obturate the holes 8 at least partially so as to constitute stops for the heads 11 of the screws.

In the embodiment shown in FIGS. 1 to 4, the mobile flap 16 is of the rotating or turning type and is guided in a pivoting movement about an axis X extending substantially perpendicularly to the connection plate 2. In a preferred embodiment, the mobile flap 16 is equipped with a central ring 19 which is engaged in a bore 21 made on the connection plate 2. As is shown more precisely in FIG. 3, the ring 19 is crimped from the posterior face 6 of the plate 2. According to to a preferred characteristic, the crimping effected is of the tight type, i.e. a friction appears between the mobile flap 16 and the connection plate 2.

In the embodiment illustrated in FIGS. 1 to 4, the mobile flap 16 comprises arms 23, in a number equal to the number of holes 8, namely four in the example illustrated. The arms 23 extend substantially in a common plane which, in the example illustrated, is substantially parallel to the connection plate 2. In this way, the plane of extension of the mobile flap 16 presents an incurved profile complementary of the incurved profile of the connection plate 2. The arms 23 of the flap 16 extend radially from the central ring 19 and are offset angularly with respect to one another in order, in the first position $P_1$, to free the cross-section of passage of the holes 8 and, in the second position $P_2$, to obturate the holes 8 at least partially. Each arm 23 preferably presents a length or an extension adapted to come in position $P_2$, at least to extend along a radius of the hole 8. In this way, the arms 23 can constitute stops for the heads 11 of the screws 9.

According to the another characteristic of the invention, the mobile flap 16 is equipped with a member 25 for receiving a tool for control in displacement ensuring passage of the mobile flap 16 from the first position $P_1$ to the second position $P_2$, and vice versa. In the embodiment illustrated, the receiving member 25 is constituted by a central orifice of prismatic shape made in the bore of the ring 19.

Figure 5:
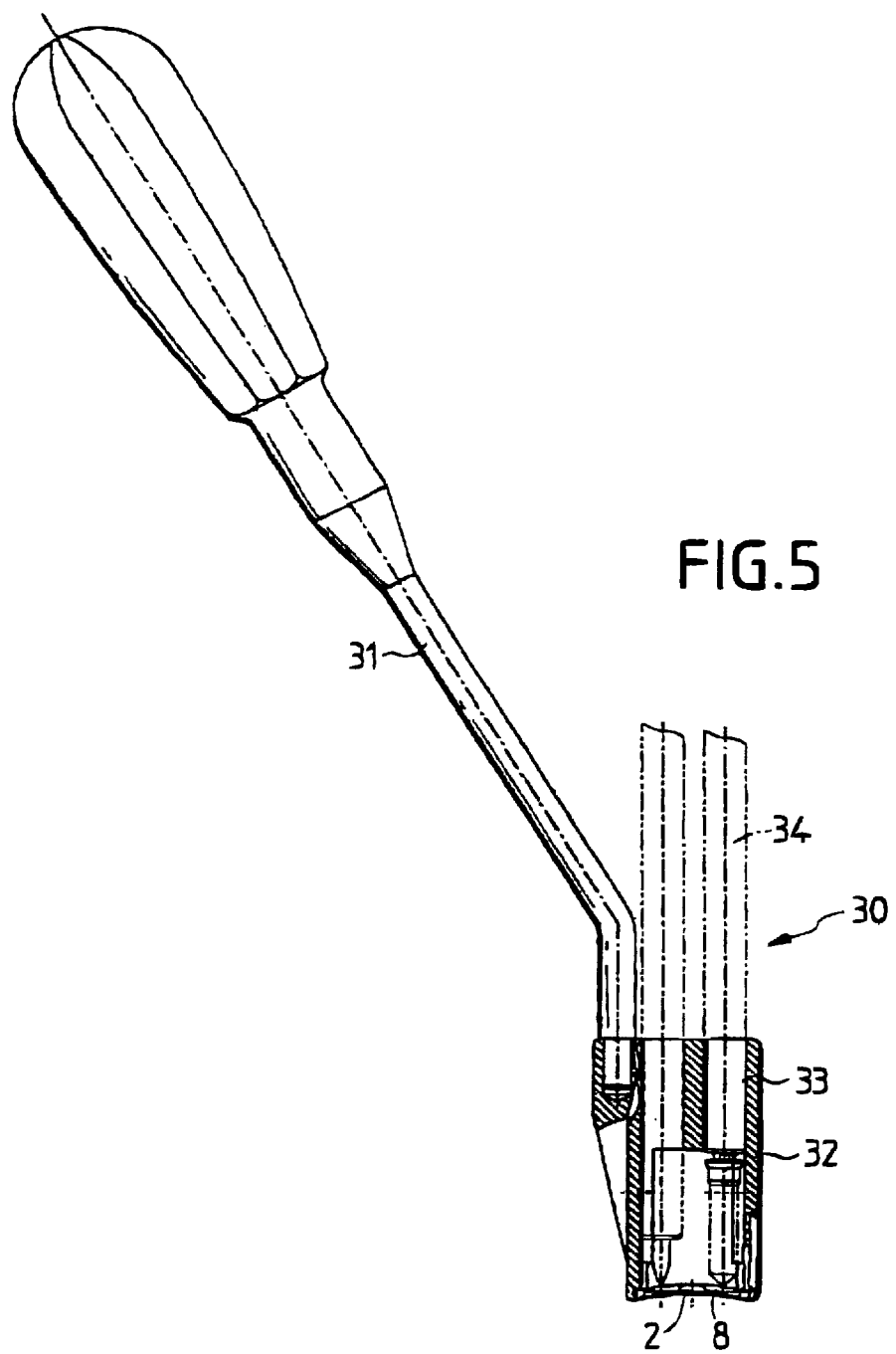
FIG. 5 is a partial elevational section of an instrument for positioning a plate according to the invention.
Figure 6:
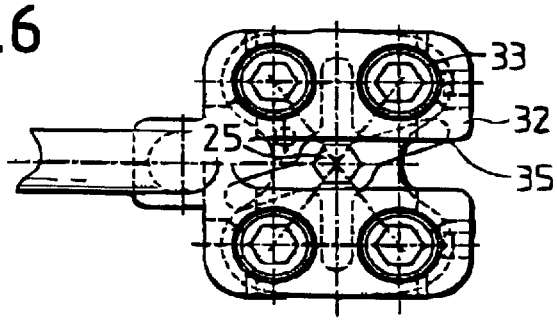
FIG. 6 is a plan view of the instrument illustrated in FIG. 5.

As appears more precisely in FIGS. 5 and 6, the connection device 1 according to the invention is intended to be positioned with the aid of an instrument 30 comprising a handle 31 removably mounted on a guide block 32 designed to bear the plate 2 from its lower face with the aid, for example, of clipping devices. The guide block 32 comprises a series of bores 33 made so as, in position of superposition with the osteosynthesis plate 2, to be in registry with the holes 8 of the plate. In this way, the block 32 makes it possible to guide, with the aid of the bores 33, diverse tools 34 ensuring positioning of the plate and shown schematically. The guide and block 32 also comprises a window 35 for guiding, extending over the whole height of the block to open out on the lower and upper faces of the block. This window 35 is arranged to allow, in position of assembly or of superposition of the device 1 on the block 32, access to the receiving member 25 and passage of the tool for controlling displacement of the mobile flap 16.

Implementation of the connection device 1 according to the invention follows directly from the foregoing description.

In order to be positioned on the vertebrae of a patient, the connection plate 2 is mounted, for example by clipping, on the guide block 32. The mobile flap 16 is placed so as to occupy its position $P_1$ freeing the cross-section of passage of the holes 8. The conventional operations of positioning the anchoring screws on the vertebrae may thus be carried out. After the operation of positioning the anchoring screws, the mobile flap 16 is intended to be controlled in rotation with the aid of an appropriate control tool which passes through the guide window 35 to engage in the receiving member 25 presented by the mobile flap 16. Rotation of the control tool ensures passage of the mobile flap 16 from position $P_1$ to position $P_2$ in which the arms 23 are in position of superposition with the heads 11 of the screws. Each arm constitutes a stop for a screw head preventing avulsion or extraction thereof. In this way, there is no clearance between the screws 9, the connection plate 2 and the body of the vertebrae. The anti-extraction device 15 according to the invention is relatively simple and quick to deploy, while being safe both during and after they have been placed in position.

According to a preferred embodiment, the connection device 1 according to the invention comprises a stop element 40 for stopping the mobile flap 16 in the position of blocking $P_2$ of the screws 9. In the example illustrated, the stop element 40 comprises a device for limiting the pivoting of the mobile flap 16. As is more precisely apparently in FIGS. 1 and 4, the plate 2 comprises, as the stop element 40, a lug or a stud placed on the path of at least one of the arms 23 to ensure abutment of an arm and, consequently, the placing of the arms in position of superposition with respect to the heads 11 of the screws. The stop stud or stop element 40 thus serves as reference stop for positioning the mobile flap 16 in its screw-blocking position $P_2$. It should be noted that, in a preferred variant embodiment, the stop device 40 is constituted not only by blocking means, of the obstacle type, but also by a the friction type blocking device constituted by the tight crimping of the mobile flap 16 on the connection plate 2. According to this variant embodiment, the mobile flap 16 is blocked, in position $P_2$, in its two directions of rotation.

In the foregoing description, the mobile flap 16 is of the rotating type, but it is clear that the use of a sliding flap may be envisaged, or one moving in rectilinear manner from a control which is either rectilinear or pivoting, converted into a linear displacement.

Figure 7:
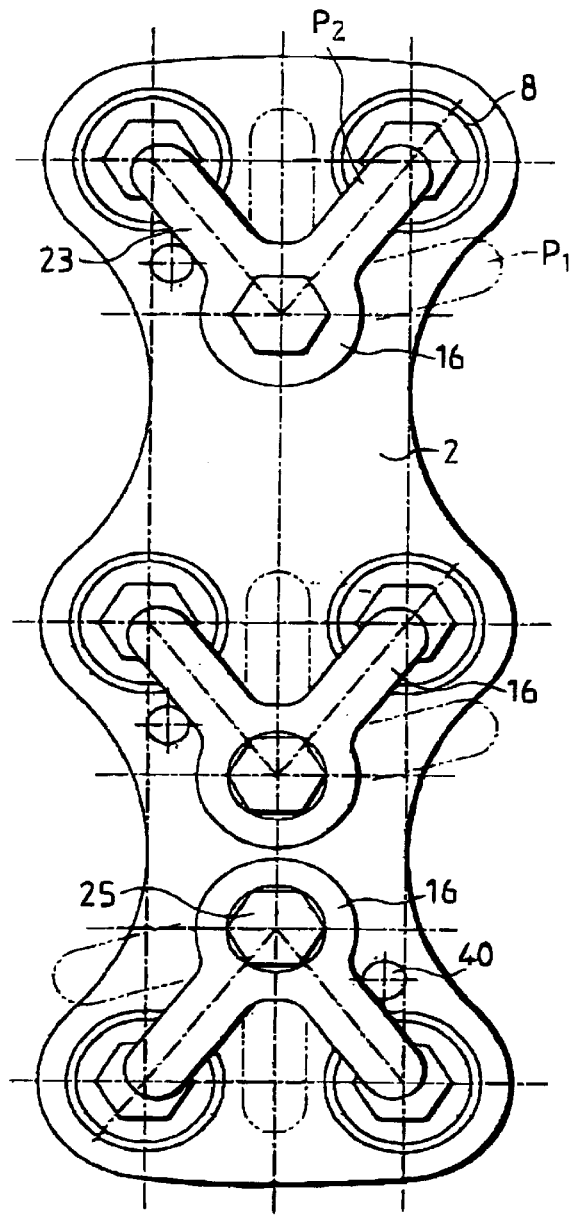
FIG. 7 illustrates the use of a connection devices for assembling three vertebrae.

In the same sense, the mobile flap 16 may be composed of one or more parts as a function of the dimensions of the connection plate 2 and of the arrangement of the holes 8. FIG. 7 illustrates another embodiment in which the connection device 2 comprises three pairs of holes 8 allowing the assembly of three contiguous vertebrae. In this embodiment, each mobile flap 16 presents solely two arms 23 offset angularly with respect to each other in order, in the first position $P_1$, to free the cross-section of passage of the holes 8 and, in the second position $P_2$, to bock the head 11 of the screws in order to prevent extraction thereof. In the same sense, it must be considered that the mobile flap 16 may be adapted to block one sole screw head. Such a variant is advantageous when the connection plate 2 comprises only two holes for the passage of connection screws between two contiguous vertebrae. Such a plate is possible in particular when it is equipped with a cage intended to occupy the intervertebral space.

Figure 8:
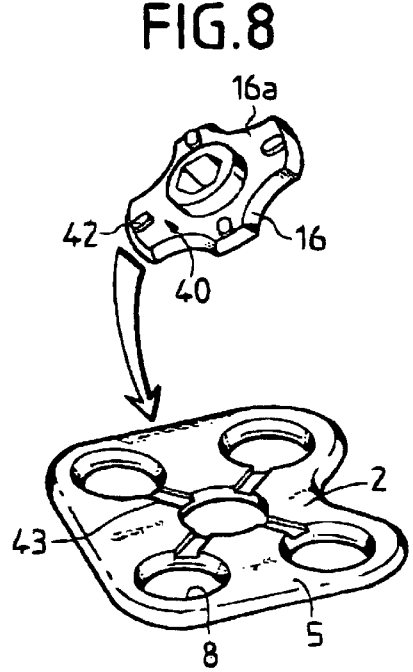
FIG. 8 is a view in perspective showing another embodiment of an intervertebral connection device according to the invention.
Figure 9:
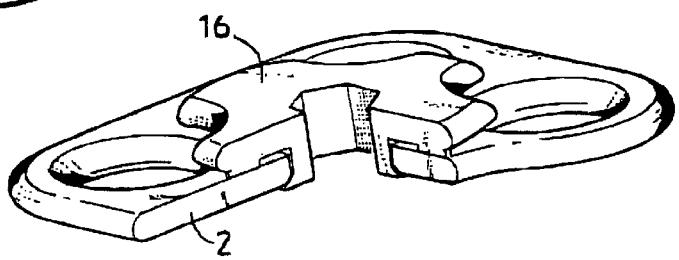
FIG. 9 is a partial sectional view showing a characteristic detail of the connection device according to FIG. 8.

FIGS. 8 and 9 illustrate another variant embodiment in which stop device 40 for stopping the mobile flap 16 is arranged for blocking the flap in its two directions of rotation. According to this example, the mobile flap 16 is equipped on its inner face 16a directed towards the anterior face 5 of the plate, with at least one and, for example, with four studs 42 in abutment on the anterior face 5 when the mobile flap 16 occupies its position $P_1$ of free access to the holes 8. Each stud 42 is intended to be engaged in a complementary housing 43 made from the anterior face 5 of the plate and located so that the stud 42 and the housing 43 cooperate when the mobile flap 16 occupies the position $P_2$ preventing extraction of the screws. The mobile flap 16 is therefore blocked in its two directions of rotation.

the present invention is by no means restricted to the above-described preferred embodiments, but covers all variations that might be implemented by using equivalent functional elements or devices that would be apparent to a person skilled in the art, or modifications the fall within the spirit and scope of the appended claims.

What is claimed is:

1. An intervertebral connection device comprising:
    a rigid osteosynthesis plate adapted to cover outer faces of at least two consecutive vertebrae at least partially, said plate comprising an anterior face and an opposite posterior face, the posterior face positionable against outer faces of at least two consecutive vertebrae, said plate further comprising at least one pair of through bores each adapted to receive an anchoring screw arranged to anchor said plate on a vertebrae, the anchoring screws each comprising a screw head;
    an anti-extraction device adapted to prevent extraction of the anchoring screws, said anti-extraction device mounted on the anterior face of said plate and acting as stops for the screw heads of the anchoring screws, said anti-extraction device comprises at least one mobile flap mounted on said plate by a guide device, said anti-extraction device is movable between a first position that permits access to the through bores and a second position that obturates access to the through bores at least partially to act as stops for the screws head; and
    a stopping element comprising a stud connected to said mobile flap, wherein said stud is adapted to engage said plate and is adapted to stop the mobile flap in a position to block the screw heads.

2. The intervertebral connection device as claimed in claim 1, wherein the stopping element elements pivoting of the mobile flap.

3. The intervertebral connection device as claimed in claim 1, wherein the stopping element is adapted to block the mobile flap in at least two pivoting directions.

4. The intervertebral connection device as claimed in claim 3, wherein the stopping element further comprises a friction type blocking device.

5. The intervertebral connection device as claimed in claim 1, wherein the mobile flap is rotatable and the guide device comprise a pivot pin extending perpendicularly to the plate.

6. The intervertebral connection device as claimed in claim 1, wherein the mobile flap comprises arms in a number equal to the number of bores, the mobile flap is offset angularly with respect to one another in a first position in order to free a cross-section of passage of the bores and in a second position in order to obturate the bores at least partially.

7. The intervertebral connection device as claimed in claim 6, wherein each of the arms comprise an extension adapted to extend at least along a radius of one of the bores.

8. The intervertebral connection device as claimed in claim 6, wherein the arms extend radially from a ring crimped on the plate.

9. The intervertebral connection device as claimed in claim 1, wherein the mobile flap comprises an incurved profile complementary of an incurved profile of the plate.

10. The intervertebral connection device as claimed in claim 1, wherein the mobile flap comprises a central orifice of prismatic shape including a member or receiving a tool for controlling displacement of the mobile flap.

11. The intervertebral connection device as claimed in claim 1, wherein the stopping element further comprises a friction type blocking device.

12. An intervertebral connection device comprising:
    a rigid osteosynthesis plate adapted to cover outer faces of at least two consecutive vertebrae at least partially, said plate comprising an anterior face and an opposite posterior face, the posterior face positionable against outer faces of at least two consecutive vertebrae, said plate further comprising at least one pair of through bores each adapted to receive an anchoring screw arranged to anchor said plate on a vertebrae, the anchoring screws each comprising a screw head;
    an anti-extraction device adapted to prevent extraction of the anchoring screws, said anti-extraction device mounted on the anterior face of said plate and acting as stops for the screw heads of the anchoring screws, said anti-extraction device comprises at least one mobile flap mounted on said plate by a guide device, said anti-extraction device is rotatable between a first position that permits access to the through bores and a second position that obturates access to the through bores at least partially to act as stops for the screws heads; and
    a stopping element comprising an obstacle-type blocking device engaged with said plate and extending out of the anterior face of said plate such that when said mobile flap is rotated to the first position, said stopping element contacts an edge of said mobile flap to obstruct further rotation of the mobile flap beyond the first position.

13. The intervertebral connection device as claimed in claim 12, wherein the stopping element limits pivoting of the mobile flap.

14. The intervertebral connection device as claimed in claim 12, wherein the stopping element is adapted to block the mobile flap in at least two pivoting directions.

15. The intervertebral connection device as claimed in claim 12, wherein the mobile flap is rotatable and the guide device comprises a pivot pin extending perpendicularly to the plate.

16. The intervertebral connection device as claimed in claim 12, wherein the mobile flap comprises arms in a number equal to the number of bores, the mobile flap is offset angularity with respect to one another in a first position in order to free a cross-section of passage of the bores and in a second position in order to obturate the bores at least partially.

17. The intervertebral connection device as claimed in claim 16, wherein each of the arms comprise an extension adapted to extend along a radius of one of the bores.

18. The intervertebral connection device as claimed in claim 16, wherein the arms extend radially from a ring crimped on the plate.

19. The intervertebral connection device as claimed in claim 12, wherein the mobile flap comprises an incurved profile complementary of an incurved profile of the plate.

20. The intervertebral connection device as claimed in claim 12, wherein the mobile flap comprises a central orifice of prismatic shape including a member for receiving a fool for controlling displacement of the mobile flap.

21. The intervertebral connection device as claimed in claim 12, wherein the stopping element further comprises a friction type blocking device.

22. The intervertebral connection device as claimed in claim 12, wherein the first and second positions are reversed such that when said mobile flap is rotated to the first position of the mobile flap obturates access to the through bores at least partially to act as steps for the screw heads, and when the mobile flap is rotated to the second position, access to the through bores is permissible.

* * * * *